United States Patent [19]
Roetzer et al.

[11] Patent Number: 5,779,476
[45] Date of Patent: Jul. 14, 1998

[54] RAPID ADAPTING PRECISION TRANSFORMER FOR OCCLUSAL RESINS

[76] Inventors: Patrick Roetzer, 1085 W. K St., Benicia, Calif. 94510; Ron Verner, 9236 Whitehorn Cir., Scottsdale, Ariz. 85262

[21] Appl. No.: 846,793

[22] Filed: Apr. 30, 1997

[51] Int. Cl.$^6$ .................................................. A61C 3/06
[52] U.S. Cl. ............................................ 433/166; 433/165
[58] Field of Search ................................... 433/165, 166

[56] References Cited

U.S. PATENT DOCUMENTS

| | | | |
|---|---|---|---|
| 662,538 | 11/1900 | LeCron | 433/166 |
| 1,548,180 | 8/1925 | Brown et al. | 433/166 |
| 2,129,843 | 9/1938 | Hollmann | 433/165 |
| 2,807,264 | 9/1957 | Tuck | 433/166 |
| 4,190,958 | 3/1980 | Martin et al. | 433/165 |
| 4,613,307 | 9/1986 | Neumeyer | 433/166 |
| 5,261,818 | 11/1993 | Shaw | 433/166 |

FOREIGN PATENT DOCUMENTS

| | | |
|---|---|---|
| 17272 | of 0000 | Germany . |
| 566538 | 12/1932 | Germany . |
| 5-309102 | 11/1993 | Japan . |

OTHER PUBLICATIONS

Militex Laboratory and Lathe Carbon Burs; Undated Publication; Miltex Instrument Company, New York.
Militex Burnishers, Amalgam Pluggers; Undated Publication, p. 80, Militex Instrument Company, New York.
Brassler USA Dental Rotary Instruments Laboratory Wall Chart,Undated, Brasseler USA, Inc., Savannah, GA.
Turbine Assortment; Undated; Author Unknown.
Busch Burs in Tungsten Vanadium Steel, Undated, Busch Bur, Germany.
Busch Bur Catalog No. 12, Undated, Pfingst & Company, Inc., New York.
A Bur!, Journal of American Dental Association, vol. 77, no. 2, p. 435, Aug. 1968.

*Primary Examiner*—John J. Wilson
*Attorney, Agent, or Firm*—John P. O'Banion

[57] ABSTRACT

A self-limiting dental composite restoration sculpting bur particularly adapted for sculpting occlusal resins. Because of the cuspal angle of its cutting surface, the bur will make cuts that closely match the naturally occurring topography of human teeth as well as provide a visual stop that indicates when the desired cutting depth has been reached. The apparatus also includes a diamond coated cutting surface that is of such a roughness that it creates a physical stop that sends a tactile response to the operator when the bur contacts enamel. This tactile response ensures that the operator can avoid overcutting the restoration. In addition, a non-diamond coated annular band can be provided on the cutting head to create a safe zone which serves a further limit stop. The bur is mounted on a straight shaft to allow maximum vertical adjustment when mounted to a standard dental drill. The advantages include a visual depth stop, a physical stop, a shape that matches naturally occurring topography, and using a straight shaft to maximize vertical adjustability.

21 Claims, 4 Drawing Sheets

RAPID ADAPTING PRECISION TRANSFORMER FOR OCCLUSAL RESINS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1 Field of the Invention

This invention pertains generally to devices and methods for restoring damaged teeth, and more particularly to a rapid adapting precision transformer for occlusal composite resins and proceleins that is particularly adapted to sculpting composite resins used to reconstruct damaged molars and bicuspids. The invention can also be used by dentists to rapidly sculpt harmonious functional occlusion on badly worn removable dentures and cemented porcelain or composite covered crowns.

2. Description of the Background Art

When a person's tooth is badly damaged by decay or injury, a dentist can either remove or repair the tooth. If the dentist chooses to repair the tooth, the damaged portions must first be cut away. Generally the dentist will remove the damaged portion of the tooth with an enamel cutting bur. When the damaged portion is removed, a cavity is generally left in its place. To fill the cavity and reconstruct the tooth, a form is placed around tooth and an amalgam or occlusal composite resin, in a soft stage, is packed into the form. Once the amalgam or composite resin has hardened, the form is removed, and hardened amalgam or composite resin remains. Because the hardened material was molded by the form, the occlusal surfaces do not usually mirror those of a natural tooth. Therefore, it is necessary for the dentist to create a topography in the reconstructed tooth that will cooperate with the other corresponding opposing teeth and perform the normal functions of human teeth.

Various cutting burs have been developed to aid dentists in removing decayed or damaged enamel from teeth. Other devices have been developed to aid dentists in shaping amalgam, which is carveable with bladed hand instruments. Composite resins, on the other hand, are hard like porcelain when ready to be sculpted. Although many dentists today use older, enamel cutting burs to sculpt dental composite restorations such as occlusal resin composite restorations, these burs have proven deficient for a number of reasons.

For example, because occlusal resins have different mechanical material properties than enamel, enamel cutters behave differently when cutting occlusal resins. Generally, enamel cutting burs cut through occlusal resins quite rapidly, which makes it more difficult to control the cutter when shaping an occlusal resin composite restorations. Another common problem is that enamel cutters have a tendency to "walk" when cutting resins, i.e., the bur tends to pull itself through the material thereby making it more difficult to control the resulting shape of the composite restoration. A further problem is that when attempting to sculpt a composite restoration with a difficult to control enamel cutter, the operator may inadvertently remove enamel or more enamel than intended, which is referred to as "overcutting". Another problem is that existing bur designs are not shaped to conveniently recreate the natural topography of bicuspids and molars.

Typical enamel cutters either cut too deeply or too shallowly when sculpting the topography of the composite restorations. For example, FIG. 1 shows a typical diamond coated bur 10 having a concave cutting surface 12. This bur is too narrow in relation to the cuspal angle of the tooth 14 and, as a result, will cut too deeply into the tooth and leave a narrow channel. Furthermore, the concave cutting surface 12 will not leave straight planes and, therefore, will not preserve the zenith of adjacent planes. On the other hand, FIG. 2 shows a bur 16 with a cutting surface 18 that is so broad in relation to the cuspal angle of the tooth 14 that the bur will undercut the tooth and destroy the cusp 20.

Therefore, using a conventional enamel cutting bur to sculpt a resin composite reconstruction requires a substantial amount of time and effort. Yet another drawback is that many enamel cutters are mounted on tapered shafts which eliminate the option of adjusting the axial placement of the cutter within the retention chuck on a high speed handpiece. In order to sculpt posterior molar composite restorations where the vertical clearance inside the mouth is limited, it is desirable to install the bur in the chuck such that as little of the bur extends outward from the chuck as possible. However, conventional burs with a taper just below the shoulder of the cutting tip will not allow proper squeezing on the shaft by the retention chuck.

Accordingly, there is a need for a rotary sculpting bur which is shaped to match the occlusal angle found in the natural topography of molars and bicuspids, which can easily and controllably cut occlusal resins, which has a visual stop for gauging the proper depth of cut for bicuspid and molar topography, which produces a tactile response when it contacts enamel so that the operator can avoid inadvertently removing enamel, and which is mounted on a uniform straight shaft which allows the bur to be axially adjusted for minimum vertical height in the retention chuck of a high speed handpiece without compromising the grip quality of the chuck. The present invention satisfies those needs, as well as others, and overcomes the deficiencies inherent in conventional rotary sculpting burs.

BRIEF SUMMARY OF THE INVENTION

The present invention generally comprises a self-limiting occlusal resin sculpting rotary bur which easily and controllably cuts occlusal resins, is shaped to conveniently recreate the topographical protrusions naturally occurring on human teeth, includes means for creating a visual depth stop to prevent cutting too deeply into the tooth being repaired, includes means for creating a tactile response when the bur contacts enamel while sculpting, and is mounted on a straight shaft thereby allowing axial adjustability when inserted in a standard dental drill chuck. More particularly, the invention comprises a diamond particle coated, acorn-shaped rotary cutting bur which has an upper surface and a lower conical cutting surface, and which is mounted on a straight shaft for use on standard high speed dental drills.

By way of example, and not of limitation, the cuspal angle of the lower conical cutting surface closely matches the naturally occurring cuspal angle found on human bicuspids and molars. Hence, the bur can be used to make cuts that match the natural topography of the remaining enamel left on the tooth that is being repaired, as well as the topography of the patient's other teeth. This substantially simplifies the work for the dentist because most or all of the sculpting work is done with the bur aligned vertically, rather than requiring the dentist to create a cuspal angle by moving a side cutting bur horizontally.

As a result of the bur having a cuspal angle, the bur cuts a cuspal angle into the restoration that matches the naturally occurring cuspal angle. This creates a "limit stop" effect that tells the dentist when he or she has cut deeply enough into the resin as indicated when the angle of the cut or the plane cut matches the cuspal angle and the tooth plane is collinear with the composite plane. In other words, the shoulder of the bur will actually "bump" into the enamel rim of the surface margin of the tooth. This effect avoids "overcutting" and removing tooth enamel instead of resin. It also limits the amount of final adjustment to be made with carbon papers and the like that the patient bites into for occlusal adjustment.

In addition, the bur includes means for producing a tactile signal when it contacts enamel. This is achieved by coating the cutting surface with very fine diamond coating such that the bur will cut through occlusal resins easily, but experience resistance when it hits enamel. This results in a tactile response that is significant enough for the dentist to easily determine that the bur is in contact with enamel, and thereby determine the proper direction to move the bur. Furthermore, the diamond coating can be excluded from the upper portion of the cutting surface so as to create a non-cutting safe zone for self-limitation on enamel.

An object of the invention is to provide a sculpting bur that can easily and controllably cut through occlusal resins.

Another object of the invention is to provide a sculpting bur that inherently makes cuts that closely match the naturally occurring topography of human teeth and thereby reduces the time required to properly sculpt a dental composite restorations.

Another object of the invention is to provide a sculpting bur that includes a visual depth stop to signal the operator that the proper depth has been reached.

Another object of the invention is to provide a sculpting bur that produces a tactile response when it contacts enamel, thereby signaling the operator that the bur is in contact with enamel.

Another object of the invention is to provide a sculpting bur that is axially adjustable on standard dental drills.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
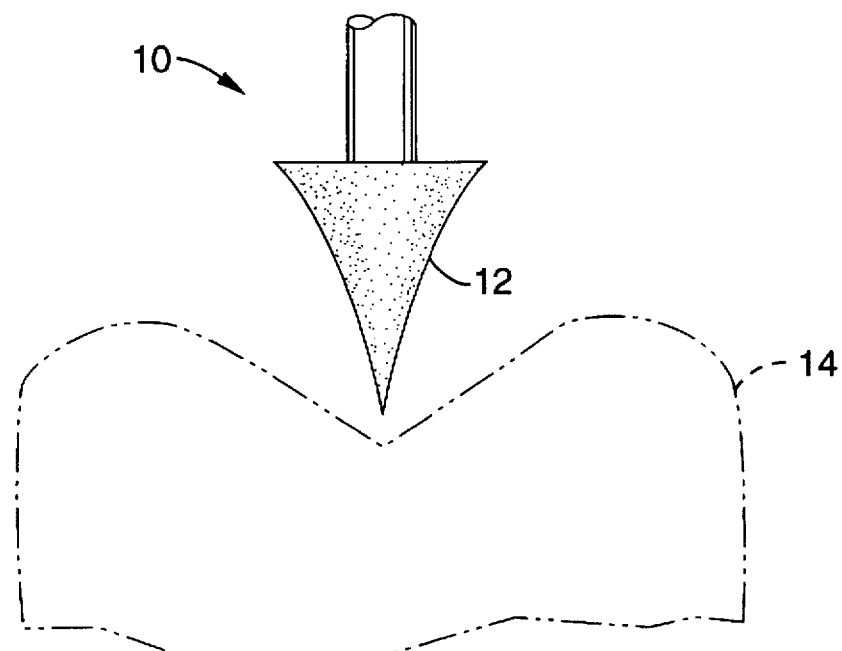
FIG. 1 is a side elevation view showing a deep, narrow cut being made in a tooth using a prior art diamond coated drill bit.
Figure 2:
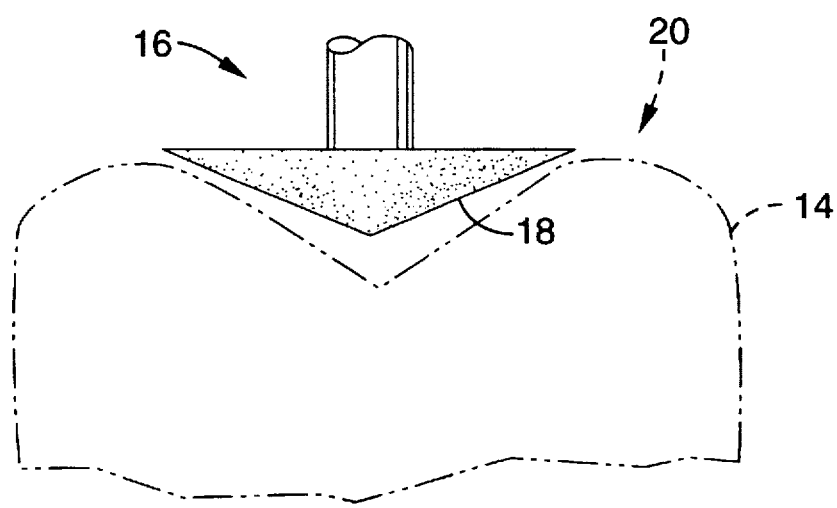
FIG. 2 is a side elevation view showing an overcut being made in a tooth using a prior art shallow drill bit.
Figure 3:
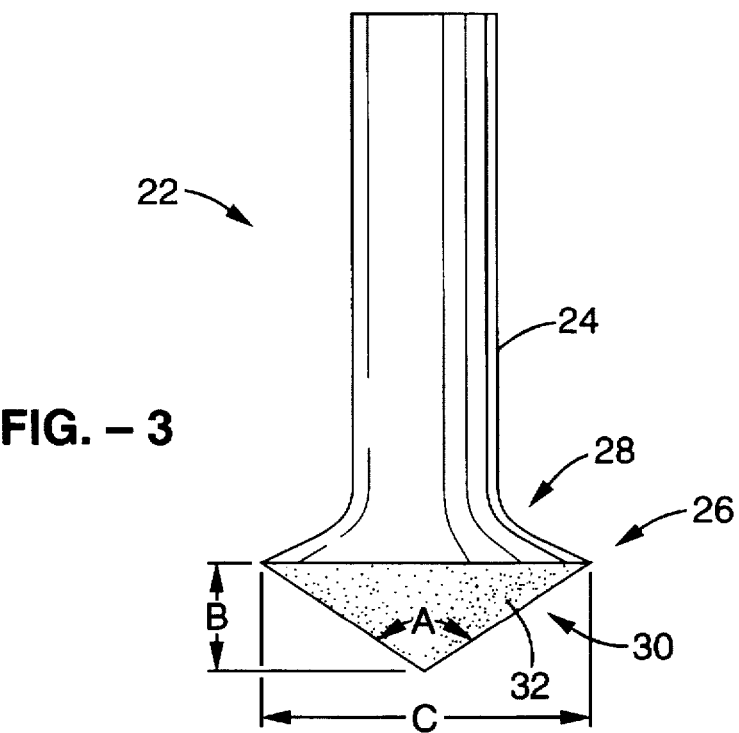
FIG. 3 is a side elevation view of the sculpting bur in accordance with the invention
Figure 5:
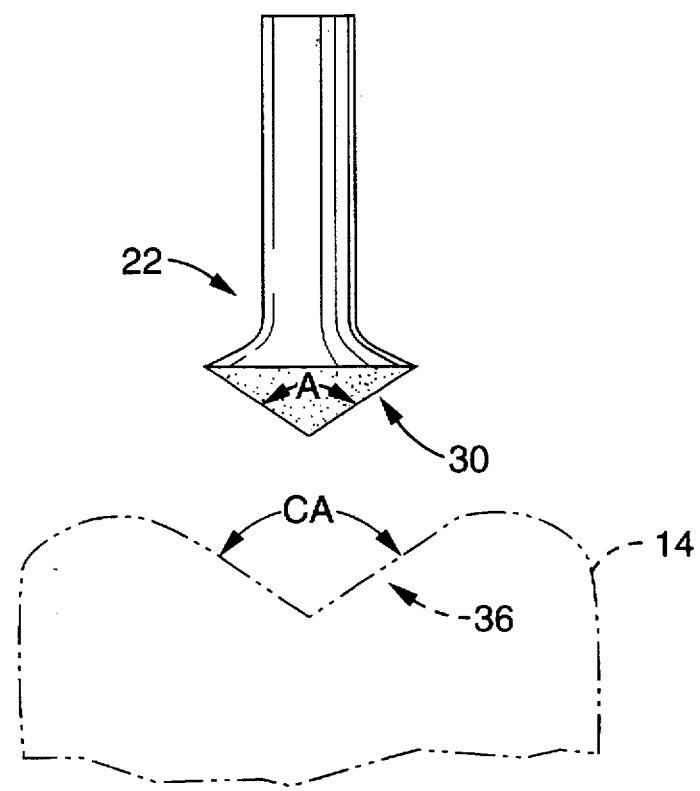
FIG. 5 is a side elevation view of the sculpting bur shown in FIG. 3 positioned in relation to the cuspal planes of a tooth shown in phantom.

Referring more specifically to the drawings, for illustrative purposes the present invention is embodied in the apparatus generally shown in FIG. 3 though FIG. 5. It will be appreciated that the apparatus may vary as to configuration and as to details of the parts without departing from the basic concepts as disclosed herein.

Referring first to FIG. 3, a sculpting bur in accordance with the present invention for sculpting occlusal resin dental composite restorations is generally shown. Sculpting bur 22 generally includes a shaft 24 and an associated "acorn-shaped" cutting head 26. Cutting head 26 generally comprises an upper portion 28, lower portion 30 and diamond coating 32. Lower portion 30 has cuspal angle "A", height "B" and diameter "C".

Note that shaft 24 has a straight configuration rather than being tapered. An important feature of the invention is that the shaft can be made grossly shorter than a tapered shaft and still fit into the collet of a standard dental handpiece. By using a shorter shaft, the present invention can be used easily in a vertical orientation. This makes access to second molars more feasible, when working on patients who are jaw opening compromised, such as arthritic patients. Conventional burs with tapered shafts promote overtightening of the collet or chuck with resultant damage due to overconstriction near the head of the bur.

In order to make cuts that closely match the cuspal angles that naturally occur in the topography of human teeth, lower portion 30 is generally conical in shape and has a cuspal angle "A" that defines the conical taper of cutting head 26. Cuspal angle "A" generally ranges between approximately 90 degrees and approximately 100 degrees, and preferably ranging from approximately 95.97 degrees to approximately 96.37 degrees, so as to be very close to the cuspal angle naturally occurring in the occlusal topography of human teeth.

Figure 4:
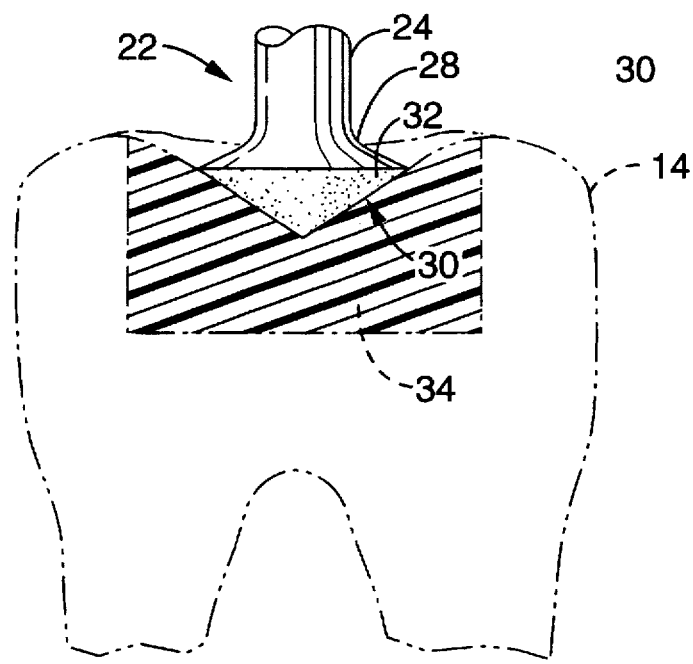
FIG. 4 is a side cross-sectional view of the sculpting bur shown in FIG. 3 positioned for cutting a composite restoration shown in phantom.

Referring also to FIG. 4, height "B" corresponds to the depth of the naturally occurring topography of human bicuspids (not shown) and molars 14. When a dentist is sculpting a hardened restoration 34 with bur 22 rotating at standard operating speeds of dental drills, bur 22 is inserted into restoration 34 until the upper edge of lower portion 30 is vertically aligned with upper surface of restoration 34 as shown in FIG. 4. Height "B" typically ranges approximately 0.75 mm (0.03 inches) to 1.75 mm (0.07 inches), and preferably from approximately 1.25 mm (0.0492 inches) to 1.35 mm (0.0531 inches) which corresponds to the naturally occurring depth of human molars.

Diameter C is the natural geometric result of angle A and height B and, for the dimensions and angular relationships given above, ranges from approximately 2.79 mm (0.110 ) inches to 3.0 mm (0.118) inches.

Referring also to FIG. 5, note that the unique cuspal angle of bur 22 provides a visual indication or "stop" that the operator can use to determine if the proper depth has been reached. This stop is provided by virtue of the angle of the cutting surface of bur 22 being approximately equal to the natural cuspal angle "CA" of the tooth. When the cutting planes of the lower portion 30 of bur 22 approximately match the cuspal planes 36 of the tooth 14, the dentist can see that the cut is sufficiently deep. This ensures that the cut is not too deep and minimizes occlusal adjustment.

In addition, in order to create a tactile response when bur 22 contacts enamel when operating on a standard dental drill, lower portion 30 of bur 22 includes a coating of diamonds 32 that are approximately forty microns in size. More specifically, the coating is a hybrid between "superfine" and "ultrafine" as those terms are of commonly used in the industry. With a diamond coating in this range, at normal handpiece speeds of approximately 100,000 to 200,000 rpm the bur cuts through occlusal resins easily but requires substantial pressure to make a significant cut into enamel. Therefore, a physical and tactile cutting stop is created. When cutting through occlusal resins, there is only slight resistance; however, when the bur contacts enamel, the cutting action slows significantly and thereby sends a tactile response to the operator. This tactile response is significant enough that the operator can easily determine that the bur is in contact with enamel, and can thereby determine the proper direction to move the bur.

Figure 6:
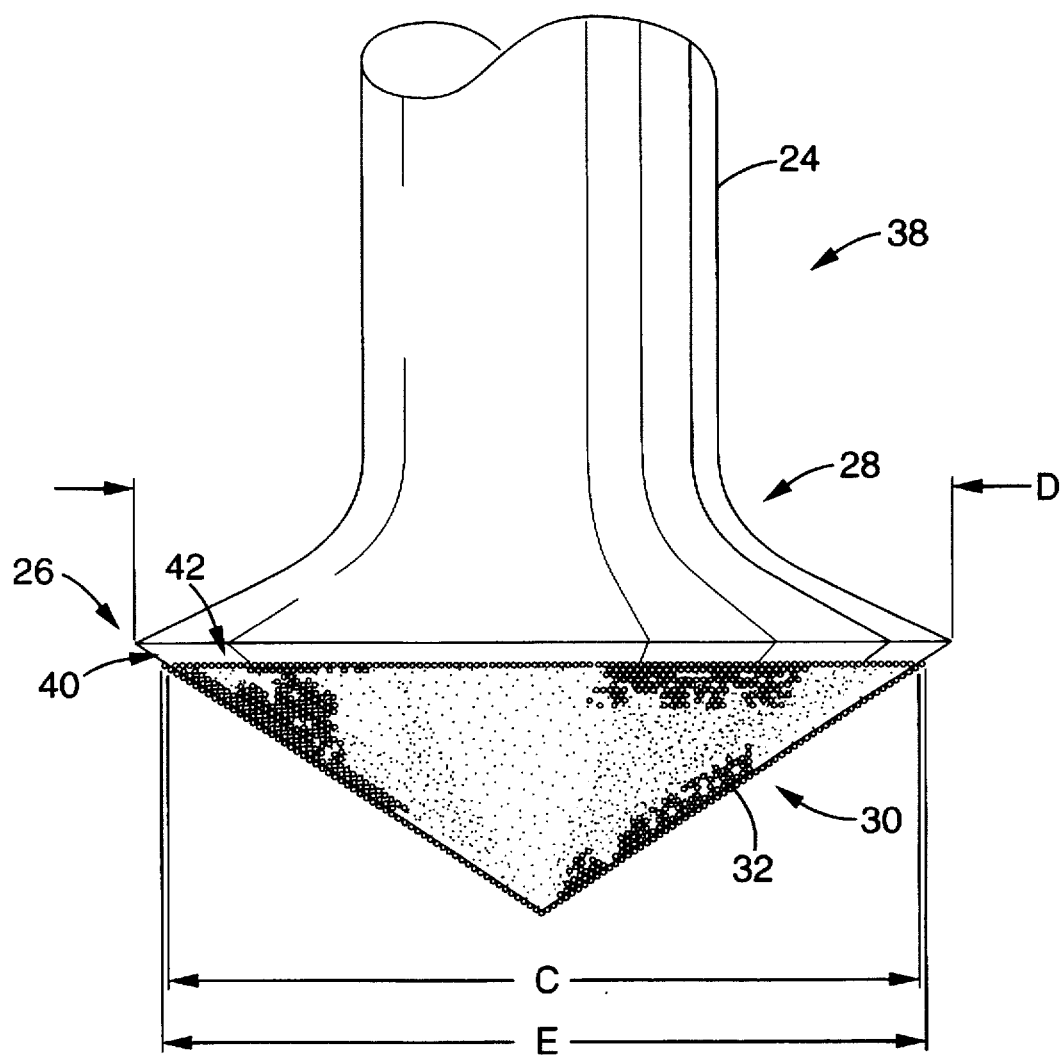
FIG. 6 is a side elevation view of an alternative embodiment of the sculpting bur shown in FIG. 3 where a safe zone is provided on the cutting head.

Referring now to FIG. 6, an alternative bur embodiment 38 is shown. In this embodiment, the diamond coating 32 does not cover the entire lower portion 30 of cutting head 26 but, instead, stops short of upper portion 28 to create an annular band or "safe zone" 40. This further facilitates a tactile limit-stop effect when enamel is contacted by safe zone 40 and /or lip 42. Preferably, the diameter "D" of lip 42 is larger than diameter "E" which is the diameter "C" of lower portion 30 of cutting head 26 plus two times the particle size of the diamonds used for the diamond coating 32. In addition, safe zone 40 preferably is on the order of approximately 0.2 mm in width.

Accordingly, it will be seen that this invention provides a simple cutting tool for sculpting dental composite restorations and particularly occlusal resin restorations. The apparatus includes a cutting head having a cuspal angle that closely matches the topography naturally found on human bicuspids and molars, includes a visual depth stop and a physical stop to prevent overcutting, and is mounted on a straight shaft in order to maximize axial adjustability when used on a standard dental drill. As a result, the invention is a rapid adapting precision transformer for occlusal resins (RAPTOR) that provides for precision sculpting not provided for by previously developed burs. In addition, the sharp tip of the bur allows for cutting secondary anatomy in the cuspal planes that the bur forms by using subtle grooves cut in elliptical shape with just the tip of the bur.

Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A rapid adapting precision transformer apparatus for occlusal resins, comprising:

(a) a shaft; and
   (b) a cutting head extending from said shaft;
   (c) said cutting head including a conical cutting surface having a cuspal angle between approximately 90 degrees and approximately 100 degrees.

2. An apparatus as recited in claim 1, wherein said wherein said cuspal angle provides visual depth stop means on said cutting head for identifying when maximum desired occlusal cutting depth has been reached during restoration of a tooth.

3. An apparatus as recited in claim 1, wherein said shaft is un-tapered.

4. An apparatus as recited in claim 1, wherein said cutting head is acorn-shaped.

5. An apparatus as recited in claim 1, further comprising tactile stop means for differentiating between contact of said cutting head with an occlusal resin and contact of said cutting head with tooth enamel during restoration of a tooth.

6. An apparatus as recited in claim 5, wherein said tactile stop means comprises a diamond coating on said cutting head.

7. An apparatus as recited in claim 6, wherein said tactile stop means further comprises a non-diamond coated band on said cutting head.

8. A self-limiting dental composite restoration sculpting bur, comprising:

(a) a shaft;
   (b) a cutting head extending from said shaft;
   (c) visual depth stop means on said cutting head for identifying when maximum desired occlusal cutting depth has been reached during restoration of a tooth; and
   (d) tactile stop means for differentiating between contact with an occlusal resin and contact with tooth enamel during restoration of a tooth.

9. A sculpting bur as recited in claim 8, wherein said visual depth stop means comprises a conical cutting surface on said cutting head having a cuspal angle between approximately 90 degrees and approximately 100 degrees.

10. A sculpting bur as recited in claim 8, wherein said visual depth stop means comprises a conical cutting surface on said cutting head having a cuspal angle ranging from approximately 95.97 degrees to approximately 96.37 degrees.

11. A sculpting bur as recited in claim 8, wherein said tactile stop means comprises a diamond coating on said cutting head.

12. A sculpting bur as recited in claim 11, wherein said tactile stop means further comprises a non-diamond coated band on said cutting head.

13. A sculpting bur as recited in claim 8, wherein said shaft is un-tapered.

14. A sculpting bur as recited in claim 8, wherein said cutting head is acorn-shaped.

15. A self-limiting dental composite restoration sculpting bur, comprising:

(a) a shaft; and
   (b) a cutting head extending from said shaft;
   (c) said cutting head including a conical cutting surface having a cuspal angle ranging from approximately 95.97 degrees to approximately 96.37 degrees.

16. A sculpting bur as recited in claim 15, wherein said cuspal angle provides visual depth stop means on said cutting head for identifying when maximum desired occlusal cutting depth has been reached during restoration of a tooth.

17. A sculpting bur as recited in claim 15, further comprising tactile stop means for differentiating between contact of said cutting head with an occlusal resin and contact of said cutting head with tooth enamel during restoration of a tooth.

18. A sculpting bur as recited in claim 17, wherein said tactile stop means comprises a diamond coating on said cutting head.

19. A sculpting bur as recited in claim 18, wherein said tactile stop means further comprises a non-diamond coated band on said cutting head.

20. A sculpting bur as recited in claim 15, wherein said shaft is un-tapered.

21. A sculpting bur as recited in claim 15, wherein said cutting head is acorn-shaped.

* * * * *